(12) United States Patent
Lappin et al.

(10) Patent No.: US 9,248,022 B2
(45) Date of Patent: Feb. 2, 2016

(54) METHOD OF IMPLANTING A GLENOID DEFECT-FILLING COMPONENT

(75) Inventors: Kyle E. Lappin, Fort Wayne, IN (US); Jason M. Chavarria, Warsaw, IN (US)

(73) Assignee: DEPUY SYNTHES PRODUCTS, INC., Raynham, MA (US)

(*) Notice: Subject to any disclaimer, the term of this patent is extended or adjusted under 35 U.S.C. 154(b) by 313 days.

(21) Appl. No.: 13/431,476

(22) Filed: Mar. 27, 2012

(65) Prior Publication Data

US 2013/0261753 A1 Oct. 3, 2013

(51) Int. Cl.
*A61F 2/40* (2006.01)
*A61F 2/30* (2006.01)

(52) U.S. Cl.
CPC ........... *A61F 2/30734* (2013.01); *A61F 2/4081* (2013.01); *A61F 2002/3092* (2013.01); *A61F 2002/30736* (2013.01); *A61F 2002/30891* (2013.01)

(58) Field of Classification Search
CPC .................... A61F 2/40; A61F 2/4081; A61F 2002/30736; A61F 2002/30891; A61F 2002/3092; A61F 2/30734
USPC .......... 623/18.11, 19.11, 19.12, 19.13, 19.14, 623/20.32, 20.33, 20.34, 23.39, 23.4, 23.41, 623/23.43
See application file for complete search history.

(56) References Cited

U.S. PATENT DOCUMENTS

| | | | |
|---|---|---|---|
| 4,964,865 A * | 10/1990 | Burkhead et al. | .......... 623/19.11 |
| 4,979,957 A | 12/1990 | Hodorek | |
| 5,019,104 A | 5/1991 | Whiteside et al. | |
| 6,228,119 B1 | 5/2001 | Ondrla et al. | |
| 6,699,289 B2 | 3/2004 | Iannotti et al. | |
| 6,855,150 B1 | 2/2005 | Linehan | |
| 7,329,284 B2 | 2/2008 | Maroney et al. | |
| 7,604,665 B2 | 10/2009 | Iannotti et al. | |
| 7,892,297 B2 | 2/2011 | Caputo | |
| 7,922,769 B2 | 4/2011 | Deffenbaugh et al. | |
| 2003/0055507 A1* | 3/2003 | McDevitt et al. | .......... 623/19.11 |
| 2004/0220674 A1* | 11/2004 | Pria | ............................ 623/19.12 |
| 2008/0294268 A1 | 11/2008 | Baum et al. | |
| 2009/0204225 A1 | 8/2009 | Meridew | |
| 2010/0161065 A1 | 6/2010 | Williams, Jr. et al. | |
| 2010/0161066 A1 | 6/2010 | Iannotti et al. | |
| 2011/0137424 A1 | 6/2011 | Lappin et al. | |
| 2012/0130498 A1 | 5/2012 | Long | |
| 2012/0130499 A1 | 5/2012 | Long | |
| 2012/0277880 A1 | 11/2012 | Winslow et al. | |
| 2013/0144393 A1* | 6/2013 | Mutchler et al. | ........... 623/19.11 |

FOREIGN PATENT DOCUMENTS

EP 1952788 A1 8/2008
FR 2825263 A1 12/2002

OTHER PUBLICATIONS

European Search Report, European Application No. 13161257.4-1654, Aug. 29, 2013, 5 pages.

* cited by examiner

*Primary Examiner* — David Isabella
*Assistant Examiner* — Suba Ganesan
(74) *Attorney, Agent, or Firm* — Barnes & Thornburg, LLP (57) ABSTRACT

An orthopaedic shoulder prosthesis includes glenoid defect-filling component configured to be implanted within a defect in a glenoid of a patient. The glenoid defect-filling component includes a porous metallic body and a plurality of holes formed in the porous metallic body, the plurality of holes being arranged in a pattern to receive a number of pegs of a discrete polymer glenoid component.

18 Claims, 7 Drawing Sheets

METHOD OF IMPLANTING A GLENOID DEFECT-FILLING COMPONENT

CROSS-REFERENCE

Cross reference is made to copending U.S. patent application Ser. No. 13/431,434, entitled "Glenoid Defect-Filing Component" by Jason Chavarria and Kyle Lappin which is assigned to the same assignee as the present invention and which is filed concurrently herewith.

TECHNICAL FIELD

The present disclosure relates generally to components and methods for modifying a glenoid surface of a scapula, and more particular, to a glenoid defect-filling component and a method of implanting the glenoid defect-filling component within the glenoid surface of the scapula.

BACKGROUND

During the lifetime of a patient, it may be necessary to perform a total shoulder replacement procedure on the patient as a result of, for example, disease or trauma. In a total shoulder replacement procedure, a humeral component having a head is utilized to replace the natural head of the arm bone or humerus. The humeral component typically has an elongated intramedullary stem that is utilized to secure the humeral component to the patient's humerus. In such a total shoulder replacement procedure, the natural glenoid surface of the scapula is resurfaced or otherwise replaced with a glenoid component which provides a bearing surface for the head of the humeral component.

Glenoid components generally include a body that defines a bearing surface for receiving the head of the humeral component and a number of attachment pegs integrally formed with the body. The attachment pegs are inserted and thereafter secured into a corresponding number of holes that are drilled in the glenoid surface of the scapula by use of bone cement.

Occasionally, the glenoid surface of the scapula includes central and/or combined defects of the glenoid surface that provide a surface to which it is difficult to attach a glenoid component or that are difficult to treat surgically. Current methods of treating central and/or combined defects of the glenoid surface include bone grafting, two stage surgery, or immobilization of the joint. While these methods can be effective, they require time-intensive surgeries, multiple surgeries, and/or long recovery times.

SUMMARY

According to an illustrative embodiment, a method of filling a defect within a glenoid surface of a scapula comprises the step of implanting a porous defect-filling component into the defect, the porous defect-filling component having a number of holes defined therein. The method further comprises the step of inserting a number of pegs of a discrete polymer glenoid component into the number of holes of the implanted porous defect-filling component so as to secure the discrete polymer glenoid component to the implanted porous defect-filling component.

The polymer glenoid component includes a bearing surface configured to articulate with a natural or prosthetic head of a humerus and the inserting step includes the step of inserting the pegs of the polymer glenoid component with the bearing surface facing away from the implanted defect-filling component.

The implanting step includes the step of implanting a porous metal defect-filling component into the defect.

The implanting step includes the step of press-fitting the defect-filling component into the defect.

The implanting step includes the step of press-fitting the defect-filling component into the defect without removing any bone tissue surrounding the defect.

The inserting step comprises the step of cementing the pegs within the holes with bone cement.

The inserting step comprises the step of press-fitting the pegs into the holes.

In another illustrative embodiment, a method of filling a defect within a glenoid surface of a scapula comprises the step of implanting a porous metal defect-filling component into the defect, the porous defecting filling component having an anchor hole formed a center of the porous metal defect-filling component and a number of stabilizing holes. The method further comprises the step of securing a discrete polymer glenoid component to the implanted porous metal defect-filling component such that an anchor peg of the polymer glenoid component is received into the anchor hole of the implanted porous metal defect-filling component and a number of stabilizing pegs of the polymer glenoid component are received into the number of stabilizing holes of the implanted porous metal defect-filling component.

The polymer glenoid component includes a bearing surface configured to articulate with a natural or prosthetic head of a humerus and the securing step includes the step of securing the pegs of the polymer glenoid component with the bearing surface facing away from the implanted defect-filling component.

The implanting step includes the step of press-fitting the porous metal defect-filling component into the defect.

The implanting step includes the step of press-fitting the porous metal defect-filling component into the defect without removing any bone tissue surrounding the defect.

The securing step comprises the step of cementing the pegs within the holes with bone cement.

The securing step comprises the step of press-fitting the pegs into the holes.

In a further illustrative embodiment, a method of filing a defect within a glenoid surface of a scapula comprises the step of implanting a porous metal defect-filling component into the defect, the porous defecting filling component having a number of holes formed therein adapted to receive a discrete polymer glenoid component.

The number of holes comprises an anchor hole formed in center of the porous metal defect-filling component and a second number of stabilizing holes.

The step of implanting comprises the step of press-fitting the porous metal defect-filling component into the defect.

The step of implanting comprises the step of press-fitting the porous metal defect-filling component into the defect without removing any bone tissue surrounding the defect.

The method further comprises the step of placing cortical bone graft over the porous metal glenoid defect-filling component.

The method further comprises the step of placing canellous bone graft over the porous metal glenoid defect-filling component.

In a further illustrative embodiment, a method of filling a defect within a glenoid surface of a scapula includes the step of implanting a porous defect-filling component into the defect, the porous defect-filling component having a hole defined therein. The method further includes the step of inserting a peg of a discrete polymer glenoid component into the hole of the implanted porous defect-filling component so as to secure the discrete polymer glenoid component to the implanted porous defect-filling component.

Other aspects and advantages of the present disclosure will become apparent upon consideration of the following drawings and detailed description, wherein similar structures have similar reference numbers.

BRIEF DESCRIPTION OF THE DRAWINGS

The detailed description particularly refers to the following figures, in which.

DETAILED DESCRIPTION OF THE DRAWINGS

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout this disclosure in reference to both the orthopaedic implants described herein and a patient's natural anatomy. Such terms have well-understood meanings in both the study of anatomy and the field of orthopaedics. Use of such anatomical reference terms in the specification and claims is intended to be consistent with their well-understood meanings unless noted otherwise.

Figure 1:
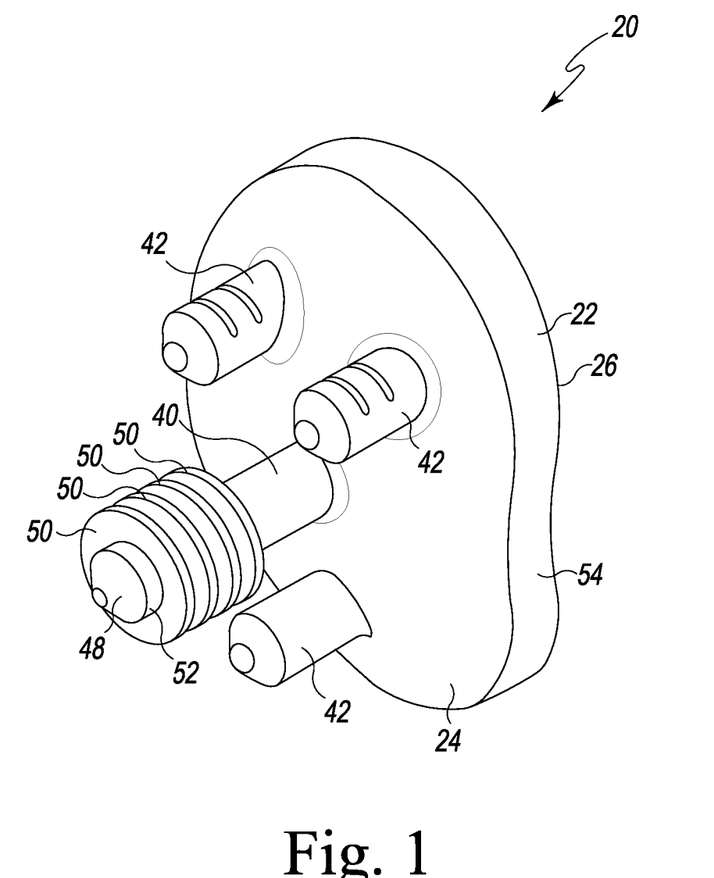
FIG. 1 is a perspective view of a glenoid component.
Figure 2:
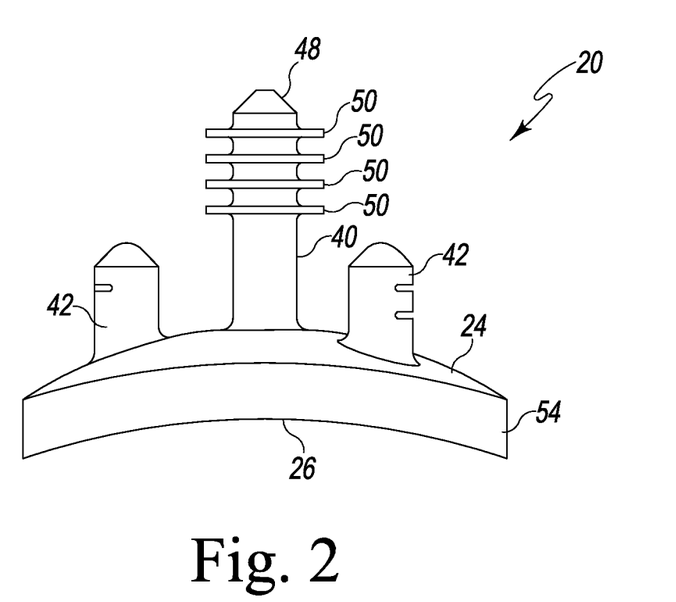
FIGS. 2 and 3 are side elevation views of the glenoid component of FIG. 1.
Figure 3:
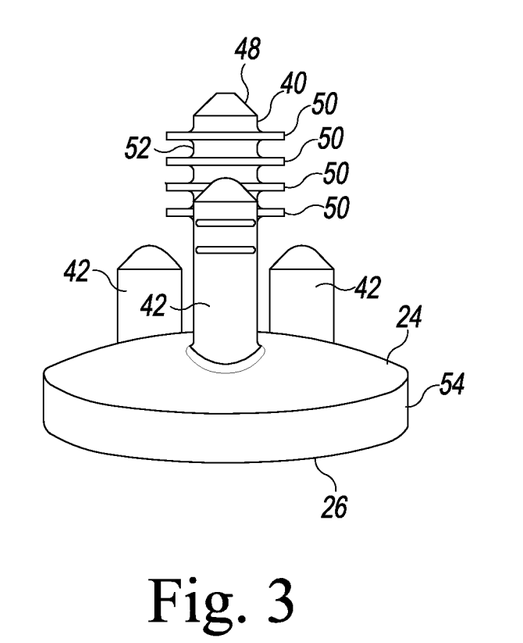

Referring now to FIGS. 1-3, there is shown a polymer glenoid component 20. The glenoid component 20 includes a body 22 having a first generally convex surface 24 and a second generally concave surface 26 opposite the convex surface 24. The convex surface 24 of the body 22 is configured to abut or otherwise contact a glenoid defect-filling component, as will be discussed in greater detail hereinafter. The concave surface 26 of the body 22 provides a smooth bearing surface upon which a natural or prosthetic humeral head 32 (see FIG. 12) articulates.

The glenoid component 20 also includes an anchor peg 40 and a number of stabilizing pegs 42 secured to and extending generally orthogonal to the convex surface 24 of the body 22. As shown in FIGS. 1-3, the anchor peg 40 includes a tapered head 48 that functions as a lead-in to facilitate insertion into a hole drilled or otherwise formed in a glenoid surface 28 of a patient's scapula 30 or within a glenoid defect-filling component, as discussed in detail below. The anchor peg 40 also includes a plurality of flexible radial fins 50 extending outwardly from a top end 52 of the anchor peg 40. The fins 50 function to secure the glenoid component 20 within the glenoid surface 28 or within a glenoid defect-filling component, as discussed below.

The stabilizing pegs 42 of the glenoid component 20 are spaced between the anchor peg 40 and an outer edge 54 of the body 22. While the exact placement and number of the stabilizing pegs 42 is not crucial, the stabilizing pegs 42 prevent the body 22 of the glenoid component 20 from moving in a plane perpendicular to the anchor peg 40 and prevent rotational movement of the glenoid component 20. Generally, the stabilizing pegs 42 are shorter than the anchor peg 34. Moreover, one or more of the stabilizing pegs 42 may be shorter than the others, although other configurations may be used. While the body 22, the anchor peg 40, and the stabilizing pegs 42 of the glenoid component 20 are shown as being integral, one or more of the anchor peg 40 or stabilizing pegs 42 may be separately secured to the body 22. As one skilled in the art would understand, any number of anchor pegs 40 or stabilizing pegs 42 may be utilized, the anchor peg 40 may include any features that aid in inserting the anchor peg 42 into a hole or retaining the anchor peg 42 within a hole, and/or the placement of the anchor peg(s) 40 and/or stabilizing peg(s) 42 may be modified without departing from the scope of the present disclosure.

The glenoid component 20, which may be used with the glenoid defect-filling components described herein, may be made of a polymeric material, for example, a polyethylene. One example of a suitable polyethylene is ultrahigh molecular weight polyethylene (UHMWPE). In addition to polymers, the glenoid component 20 may be made from ceramic, metal, or a composite material. Examples of these materials include alumina, zirconia, and alumina/zirconia composite or composite material.

Figures 4, 5:
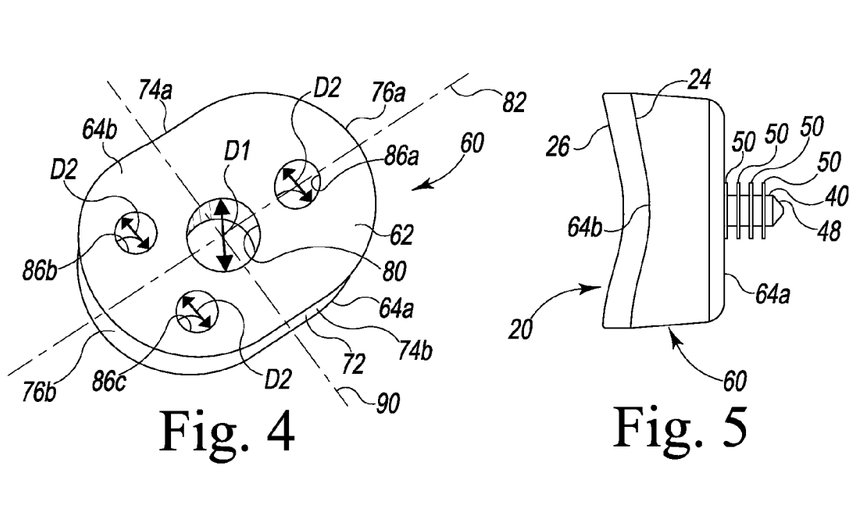
FIG. 4 is a top perspective view of a first embodiment of a glenoid defect-filling component.
FIG. 5 is a side elevational view of the glenoid defect-filling component of FIG. 4 attached to the glenoid component of FIG. 1.

A first embodiment of a glenoid defect-filling component 60 is depicted in FIGS. 4 and 5. The glenoid defect-filling component 60 has a body 62 with a medial surface 64a that is in contact with an inner surface 66 forming a defect 68 (see FIG. 10) and a lateral surface 64b that forms an attachment or restructured surface. The body 62 further includes a generally oval-shaped side wall 72 extending between the surfaces 64a, 64b and forming an outer edge of the body 60. The wall 72 includes generally straight walls 74a, 74b connected by generally round walls 76a, 76b. A primary hole 80 extends through the body 60 between the surfaces 64a, 64b. A center of the primary hole 80 is generally aligned along a longitudinal axis 82 of the body 60 and has a first diameter D1. The primary hole 80 is also disposed equidistant from each of the straight walls 74a, 74b of the body 60 and equidistant from each of the round walls 76a, 76b of the body 60.

A number of secondary holes 86a-86c extend through the body 60 between the surfaces 64a, 64b and are disposed between the primary hole 80 and the oval-shaped wall 72 of the body 60. The secondary hole 86a has a center generally aligned along the longitudinal axis 82 of the body 60 and spaced between the primary hole 80 and the round wall 76a. The centers of the holes 84b, 84c are disposed between the primary hole 80 and the round wall 76b and are further spaced outwardly of the primary hole 80 along a lateral axis 90. Each of the secondary holes 86a-86c has a diameter D2 that is less than the diameter D1 of the primary hole 80.

The size, shape, and placement of the primary hole 80 and the secondary holes 86a-86c may be varied without departing from the scope of the present disclosure. In particular, the size, shape, and placement of the holes 80, 86a-86c will be dependent upon the particular use of the glenoid defect-filling component 60 and/or, if utilized, the design and pattern of pegs of a glenoid component for use with the glenoid defect-filling component 60.

The glenoid defect-filling component 60 may have a body 62 made of an implant-grade biocompatible metal. Examples of such metals include cobalt, including cobalt alloys such as a cobalt chrome alloy (e.g., CoCrMo), titanium, including titanium alloys such as a Ti6Al4V alloy, and stainless steel. The metallic material may be coated with a porous structure, for example, a coating of cobalt-chromium alloy beads, such as a product sold by DePuy Orthopaedics Inc. under the trade mark POROCOAT®. Optionally, the external surface of the metal body 60 may be provided with a coating of an additional or alternative material that promotes bony ingrowth and/or outgrowth, such as a hydroxyapatite material. Still further, the external surface of the metal body 60 may be coated with a surface treatment, such as hyaluronic acid (HA), to enhance biocompatibility. Still optionally, the body 62 of the glenoid defect-filling component 60 may be embodied as a porous metal body in a manner similar to as described below in regard to FIG. 9.

The glenoid defect-filling component 60 of FIG. 4, or any of the other glenoid defect-filling components disclosed herein, may be utilized alone or in combination with cancellous or cortical graft to fill a defect in a glenoid surface 28 of the scapula 30 or may be used in combination with other treatments. In one exemplary embodiment, the glenoid defect-filling component 60 may be utilized in combination with an artificial glenoid component, such as the glenoid component 20 shown and discussed in relation to FIGS. 1-3. As seen in FIG. 5, once the glenoid defect-filling component 60 has been secured within the defect 68, a discrete glenoid component 20 (or any other glenoid component) may be secured to the glenoid defect-filling component 60. In particular, the anchor peg 40 of the glenoid component 20 is inserted into the primary hole 80 of the glenoid defect-filling component 60 and the stabilizing pegs 42 are inserted into the secondary holes 86a-86c. The flexible and deformable nature of the radial fins 50 extending from the anchor peg 40 allow the fins 50 to deform upon insertion of the anchor peg 40 into the primary hole 80, thereby creating resistance to extraction of the anchor peg 40 from the primary hole 80 once fully inserted therein. While the anchor peg 40 prevents removal of the glenoid component 20 from the glenoid defect-filling component 60, the stabilizing pegs 42 prevent rotational movement of the glenoid component 20 and movement of the glenoid component 20 in a plane perpendicular to the anchor peg 40.

As shown in FIG. 5, the convex medial surface 24 of the glenoid component 20 abuts the lateral surface 64b of the glenoid defect-filling component 60. In this embodiment, the lateral surface 64b of the glenoid defect-filling component 60 is shown as having a concave curvature that fits within the convex medial surface 24 of the glenoid component 20.

Figures 7, 8:
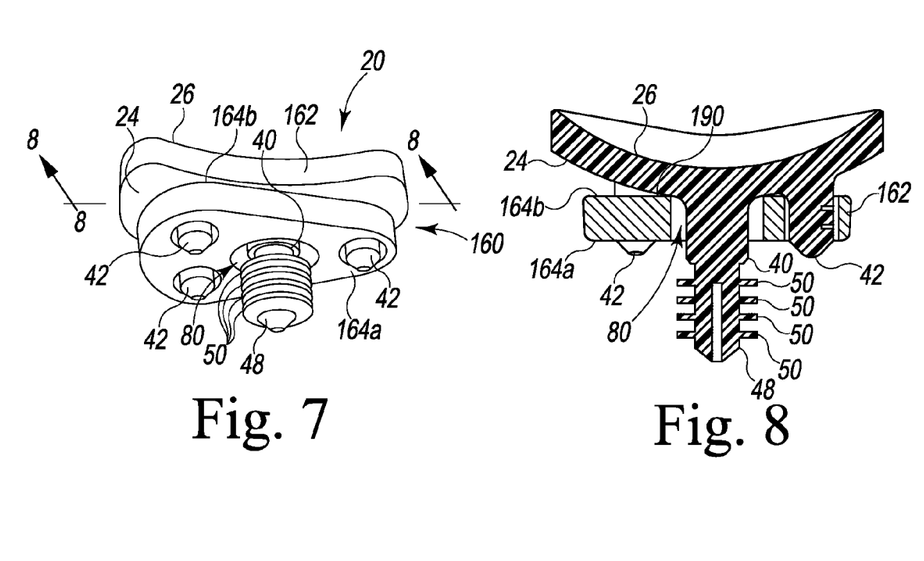
FIG. 7 is a bottom perspective view of the glenoid defect-filling component of FIG. 6 attached to the glenoid component of FIG. 1.
FIG. 8 is a cross-sectional view of the glenoid defect-filling component and glenoid component of FIG. 7 taken generally along the lines 8-8 of FIG. 7.

Optionally, and as shown in FIGS. 7 and 8, the lateral surface 64b may alternatively be planar, in which case, centers of the convex medial surface 24 and the lateral surface 64b may be in contact, but the remainder of such surfaces may be spaced apart.

Figure 6:
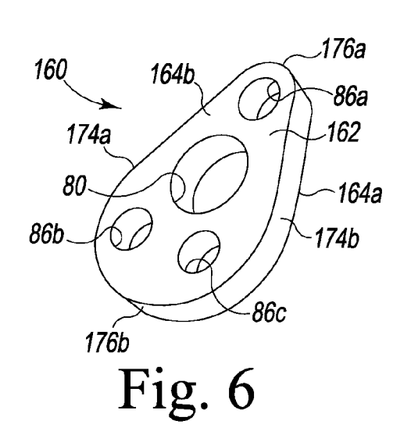
FIG. 6 is a top perspective view of a second embodiment of a glenoid defect-filling component.

Referring now to FIGS. 6-8, a second embodiment of a glenoid defect-filling component 160 similar to the glenoid defect-filling component 60 is shown. Similar elements in FIGS. 6-8 will be numbered in a similar manner as in FIGS. 4 and 5. The glenoid defect-filling component 160 includes a body 162 having a generally planar medial surface 164a that is in contact with the inner surface 66 forming a defect 68 (see FIG. 10) and a generally planar lateral surface 164b that forms an attachment or restructured surface. The body 162 further includes a connecting wall 172 extending between the surfaces 164a, 164b and forming an outer edge of the body 60. The wall 172 includes planar side walls 174a, 174b that are angled inwardly toward one another and connected by generally round walls 176a, 176b. A radius of curvature of the round wall 176a is less than a radius of curvature of the round wall 176b. The glenoid defect-filling component 160 may be made of the same materials as disclosed with respect to the glenoid defect-filling component 60.

As depicted in FIGS. 7 and 8, a polymer glenoid component, such as the glenoid component 20 of FIGS. 1-3, may be attached to and secured within the glenoid defect-filling component 160, in the same manner as discussed with respect to the glenoid defect-filling component 60. In particular, when the glenoid component 20 is attached to the glenoid defect-filling component 160, the convex medial surface 24 of the glenoid component 20 is disposed adjacent the lateral surface 164b of the glenoid defect-filling component 160. Due to the planar nature of the lateral surface 164b, only edges 190 of the lateral surface 164b adjacent the primary hole 80 contact the convex medial surface 24 of the glenoid component 20. The convex medial surface 24 is otherwise spaced apart from the lateral surface 164b. In this embodiment, prior to implantation of the glenoid defect-filling component 60 and the glenoid component 20 within the scapula 30, bone cement or graft material may be placed into the spaces between the glenoid defect-filling component 60 and the glenoid component 20, thereby providing resistance to separation of the glenoid component 20 from the glenoid defect-filling component 60, and thus, the scapula 30.

Figure 9:
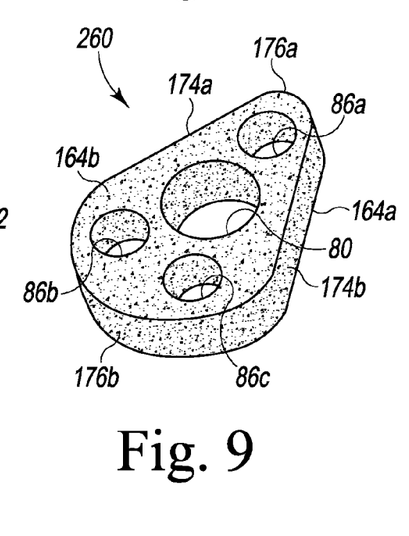
FIG. 9 is a top perspective view of a third embodiment of a glenoid defect-filling component.

Referring now to FIG. 9, a further embodiment of a glenoid defect-filling component 260 that is similar to the glenoid defect-filling component 160 is shown. The glenoid defect-filling component 260 of FIG. 9 is essentially the same as the glenoid defect-filling component 160 of FIGS. 6-8 except for the configuration of its metallic 162. Specifically, in lieu of a solid metal body with a porous coating disposed thereon, the glenoid defect-filling component 260 of FIG. 9 has a porous metal body. As such, when the glenoid defect-filling component 260 is implanted in a defect 68 within the glenoid surface 28 of the patient's scapula 30, bony ingrowth into the porous metal body will occur over time.

To construct such a porous body, metal particles, such as spherical metal particles, are mixed with particles, such as powder particles, of a sacrificial polymer and optionally a binding agent to bind the metal particles to one another. Such a mixture is then molded into the desired shape of the glenoid defect-filling component 260. Once molded into the desired shape, the sacrificial polymer is removed by water extraction. This removes the sacrificial polymer without disturbing the shape of the glenoid defect-filling component's porous metal body. The exposed portions of the porous body promote bony ingrowth or cement adhesion into the glenoid defect-filling component 260 when it is implanted in the manner similar to as described below. It should be appreciated that any desirable type of material may be used as the sacrificial polymer. One type of such material is a meltable, high molecular weight hydrophilic polymer. A specific example of one such polymer is polyethylene oxide.

It should be appreciated that the above method of constructing a porous metal body is but one exemplary process, with numerous other known processes being contemplated for use. For example, the porous metal body could be formed by sintering the metal particles into the shape of glenoid defect-filling component 260.

The glenoid defect-filling components 60, 160, 260 and any variation of glenoid defect-filling components covered by the present disclosure may be utilized alone, with a cancellous or cortical graft, or in combination with a glenoid component, such as the glenoid component depicted in FIGS. 1-3. Optionally, any glenoid component may be utilized with the glenoid defect-filling components disclosed herein (or variations thereof). In particular, the glenoid component and glenoid defect-filling component need only have peg and hole patterns, respectively, that match such that the glenoid component can be secured to the glenoid defect-filling component.

Figure 10:
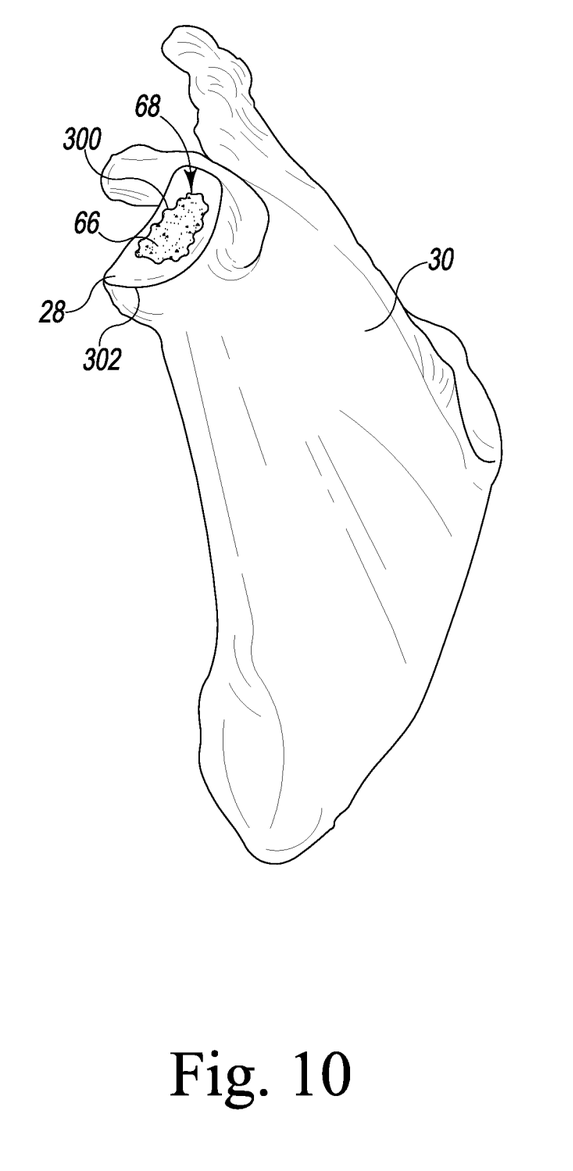
FIG. 10 is a perspective view of a scapula with a defect disposed within a glenoid surface of the scapula.

A method of filling a defect 68, such as seen in FIG. 10, within a glenoid surface 28 of a scapula 30 will now be discussed in relation to the various manners in which the glenoid defect-filling components 60, 160, 260 may be utilized.

Figure 13:
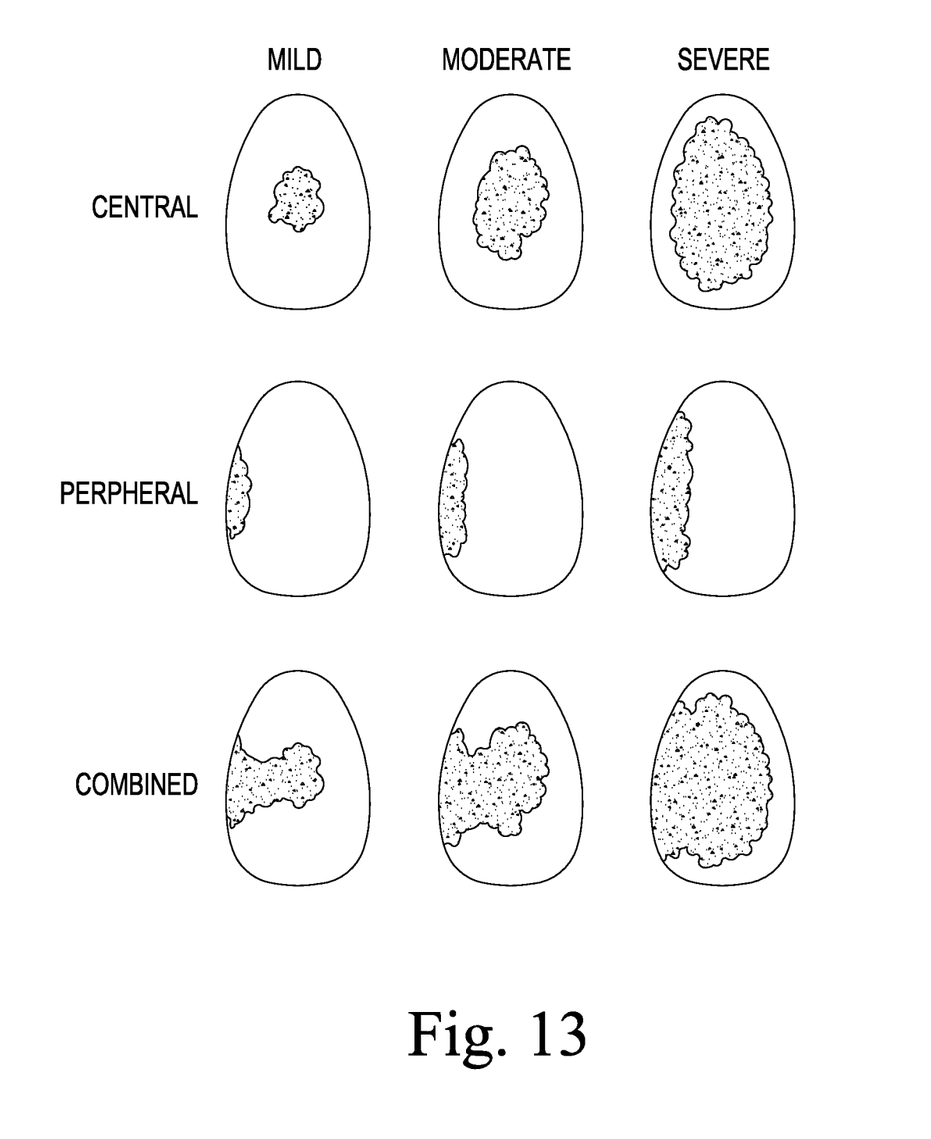
FIG. 13 is a chart depicting various types of possible defects within the glenoid surface of the scapula.

Referring to FIG. 10, the defect 68 is generally formed by the inner surface 66 and a wall 300 that forms the general shape of the defect 68. While the methods herein will be described with respect to the defect 68 as seen in FIG. 10, the methods may be utilized for any number of different defects, including those shown in FIG. 13. The wall 300 may be continuous if the defect 68 is completely contained within the glenoid surface 28 or may be discontinuous if the defect extends to an outer edge 302 of the glenoid surface 28.

Figure 11:
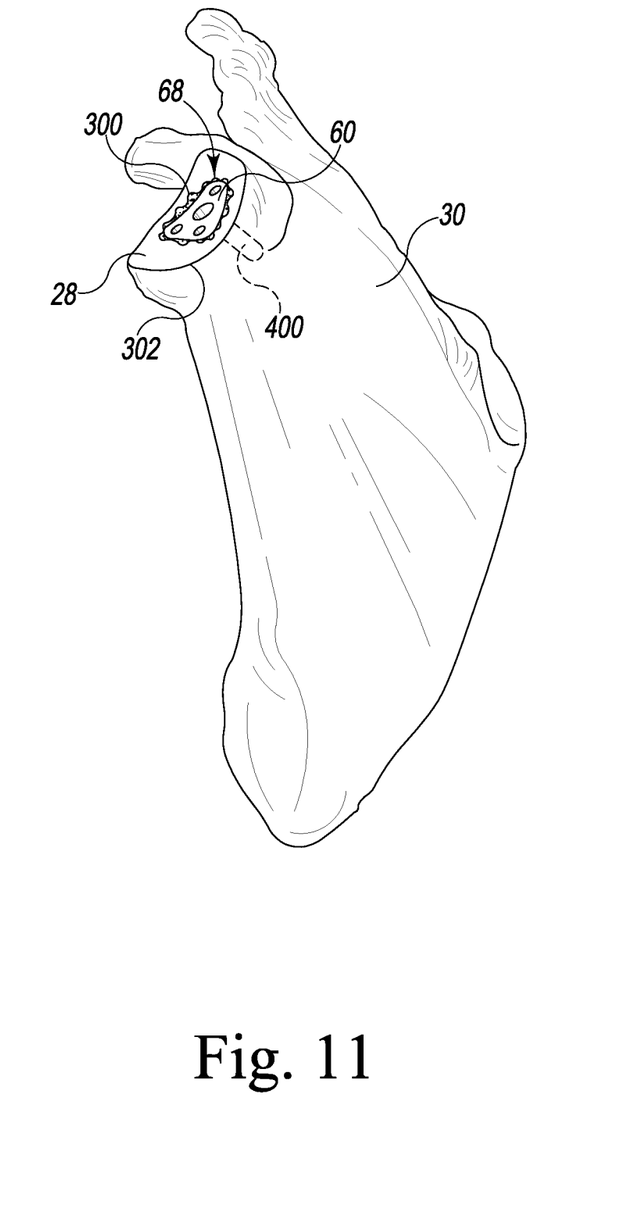
FIG. 11 is a perspective view of the scapula of FIG. 10 with the glenoid defect-filling component of FIG. 8 implanted within the defect.

An appropriate glenoid defect-filling component for a particular defect is selected based on the shape, size, and location of the defect within the glenoid surface 28. The glenoid defect-filling component, for example, the glenoid defect-filling component 60, is implanted within the defect 68, as seen in FIG. 11. The glenoid defect-filling component 60 may be secured within the defect 68 by cement (e.g., bone cement), press-fit, interference fit, or combination thereof. Optionally, the glenoid defect-filling component may be implanted within the glenoid surface 28 of the scapula 30 without removing any bone tissue surrounding the defect.

After a period of time with the glenoid defect-filling component 60 implanted within the defect 68, bony ingrowth will further secure the glenoid defect-filling component 60 to the bone tissue of the patient's scapula 30, thereby preventing the glenoid defect-filling component 60 from moving out of the defect 68. In one embodiment of the method, the glenoid defect-filling component 60 is not used with other treatments. In another embodiment, the glenoid defect-filling component 60 is used in combination with a cancellous or cortical graft, which is placed over the glenoid defect-filling component 60.

Figure 12:
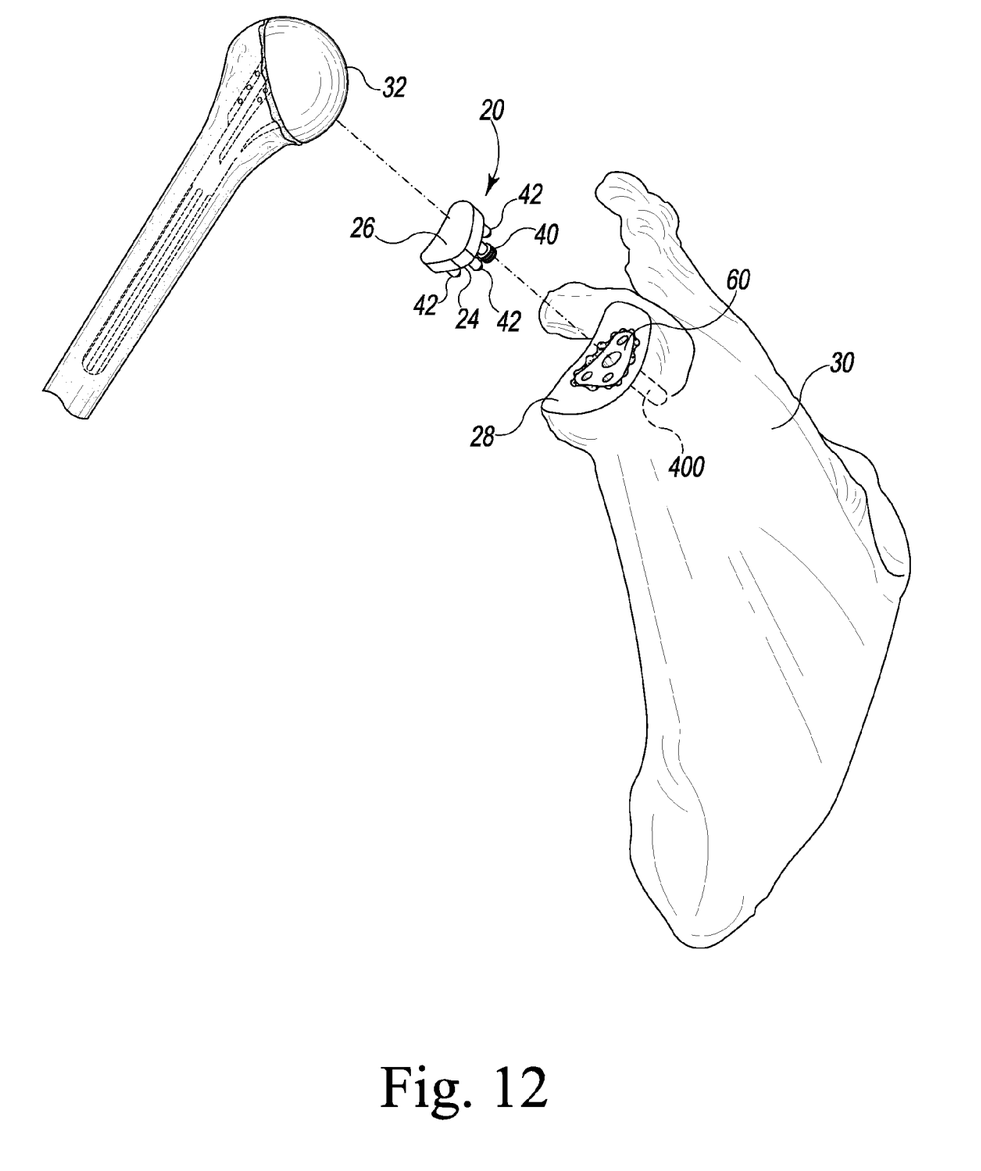
FIG. 12 is a perspective view of the scapula of FIG. 10 with the glenoid defect-filling component of FIG. 8 implanted within the defect and the glenoid component being installed within the glenoid defect-filling component.

In another embodiment of the method, as depicted in FIG. 12, after implantation of the glenoid defect-filling component 60 within the defect 68, a polymer glenoid component, such as the glenoid component 20 of FIGS. 1-3 may be secured to the glenoid defect-filling component 60. Prior to insertion of the glenoid component 20, a drill (not shown) may be used to create a bore 400, as shown in FIGS. 11 and 12, within the scapula 30 that extends deeper than the defect 68. Thereafter, the anchor peg 40 of the glenoid component 20 is inserted into the primary hole 80 of the glenoid defect-filling component 60 and into the bore 400 formed in the scapula 30, as shown in FIG. 12. The stabilizing pegs 42 are simultaneously inserted into the secondary holes 86a-86c. As noted above, the radial fins 52 on the anchor peg 40 deform upon insertion of the anchor peg 40 into the primary hole 80, thereby creating resistance to extraction of the anchor peg 40 from the primary hole 80 once full inserted therein. Optionally, the stabilizing pegs 42 may be cemented into the holes 86a-86c.

While the glenoid components and the glenoid defect-filling components shown in the figures and described in detail include multiple pegs and multiple holes, respectively, a glenoid component and a glenoid defect-filling component may alternatively include a single peg and a single hole, respectively. In such an embodiment, the hole of the glenoid defect-filling component is shaped, sized, and positioned to receive the peg of the glenoid component. The glenoid defect-filling component with a single hole may be made and implanted in the same manner as discussed with respect to the previous embodiments.

In a further embodiment, any of the glenoid defect-filling components may be formed with one or more windows or cut-outs. For example, a window may be formed within a side wall of a glenoid defect-filling component, extending inwardly to expose, for example, a peg of a glenoid component when the glenoid component is secured to the glenoid defect-filling component.

As will become apparent from reading the present specification, any of the features of any of the embodiments disclosed herein may be incorporated within any of the other embodiments without departing from the scope of the present disclosure.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the apparatus, system, and method described herein. It will be noted that alternative embodiments of the apparatus, system, and method of the present disclosure may not include all of the features described yet still benefit from at least some of the advantages of such features. Those of ordinary skill in the art may readily devise their own implementations of the apparatus, system, and method that incorporate one or more of the features of the present invention and fall within the spirit and scope of the present disclosure.

The invention claimed is:

1. A method of filling a defect within a glenoid surface of a scapula, the method comprising:
    defining a bore in the scapula that extends deeper than the defect,
    implanting a porous defect-filling component into the defect, the porous defect-filling component having a number of holes defined therein, and
    inserting a number of pegs of a discrete polymer glenoid component into the number of holes of the implanted porous defect-filling component so as to secure the discrete polymer glenoid component to the implanted porous defect-filling component,
    wherein the number of pegs includes a first peg that extends through a first hole of the number of holes, the first peg having an end positioned beyond the first hole and received in the bore defined in the scapula after the discrete polymer glenoid component is secured to the implanted porous defect-filling component.

2. The method of filling a defect of claim 1, wherein the polymer glenoid component includes a bearing surface configured to articulate with a natural or prosthetic head of a humerus and the inserting step includes the step of inserting the pegs of the polymer glenoid component with the bearing surface facing away from the implanted defect-filling component.

3. The method of filling a defect of claim 1, wherein the porous defect-filling component includes a porous metal defect-filling component.

4. The method of filling a defect of claim 1, wherein the implanting step includes the step of press-fitting the defect-filling component into the defect.

5. The method of filling a defect of claim 1, wherein the implanting step includes the step of press-fitting the defect-filling component into the defect without removing any bone tissue surrounding the defect.

6. The method of filling a defect of claim 1, wherein the inserting step comprises the step of cementing the pegs within the holes with bone cement.

7. The method of filling a defect of claim 1, wherein the inserting step comprises the step of press-fitting the pegs into the holes.

8. A method of filling a defect within a glenoid surface of a scapula, the method comprising:
   defining a bore in the scapula that extends deeper than the defect,
   implanting a porous metal defect-filling component into the defect, the porous metal defecting filling component having (i) an anchor hole formed a center of the porous metal defect-filling component, and (ii) a number of stabilizing holes, and
   securing a discrete polymer glenoid component to the implanted porous metal defect-filling component such that (i) an anchor peg of the polymer glenoid component is received into the anchor hole of the implanted porous metal defect-filling component, and (ii) a number of stabilizing pegs of the polymer glenoid component are received into the number of stabilizing holes of the implanted porous metal defect-filling component,
   wherein the anchor peg extends through the anchor hole and has an end positioned beyond the anchor hole and is received in the bore defined in the scapula after the discrete polymer glenoid component is secured to the implanted porous metal defect-filling component.

9. The method of filling a defect of claim 8, wherein the polymer glenoid component includes a bearing surface configured to articulate with a natural or prosthetic head of a humerus and the securing step includes the step of securing the pegs of the polymer glenoid component with the bearing surface facing away from the implanted defect-filling component.

10. The method of filling of claim 8, wherein the implanting step includes the step of press-fitting the porous metal defect-filling component into the defect.

11. The method of filling of claim 8, wherein the implanting step includes the step of press-fitting the porous metal defect-filling component into the defect without removing any bone tissue surrounding the defect.

12. The method of filling of claim 8, wherein the securing step comprises the step of cementing the pegs within the holes with bone cement.

13. The method of filling of claim 8, wherein the securing step comprises the step of press-fitting the pegs into the holes.

14. A method of filling a defect within a glenoid surface of a scapula, the defect being partially defined by an inner surface of the glenoid extending inwardly from the glenoid surface, the method comprising:
   implanting a porous metal defect-filling component into the defect such that a medial surface and a side wall of the porous metal defect-filling component engage the inner surface of the glenoid, the porous metal defect-filling component having (i) a lateral surface positioned opposite the medial surface, and (ii) a number of holes extending through the medial and the lateral surface that are adapted to receive a discrete polymer glenoid component, wherein the side wall extends between the lateral surface and the medial surface to form an outer edge of the porous metal defect-filling component,
   defining a bore in the scapula that extends deeper than the defect,
   inserting a number of pegs of the discrete polymer glenoid component into the number of holes of the implanted porous defect-filling component so as to secure the discrete polymer glenoid component to the implanted porous defect-filling component,
   wherein the number of pegs includes a first peg that extends through a first hole of the number of holes, the first peg having an end positioned beyond the first hole and received in the bore defined in the scapula after the discrete polymer glenoid component is secured to the implanted porous defect-filling component.

15. The method of filling of claim 14, the number of holes comprises (i) an anchor hole formed in center of the porous metal defect-filling component, and (ii) a second number of stabilizing holes.

16. The method of filling of claim 14, wherein the step of implanting comprises the step of press-fitting the porous metal defect-filling component into the defect.

17. The method of filling of claim 14, wherein the step of implanting comprises the step of press-fitting the porous metal defect-filling component into the defect without removing any bone tissue surrounding the defect.

18. A method of filling a defect within a glenoid surface of a scapula, the method comprising:
   defining a bore in the scapula that extends deeper than the defect,
   implanting a porous defect-filling component into the defect, the porous defect-filling component having a hole defined therein, and
   inserting a peg of a discrete polymer glenoid component into the hole of the implanted porous defect-filling component so as to secure the discrete polymer glenoid component to the implanted porous defect-filling component, wherein the peg extends through the hole and has an end positioned beyond the hole in the bore defined in the scapula when the discrete polymer glenoid component is secured to the implanted porous defect-filling component.

\* \* \* \* \*